United States Patent [19]

Peuker et al.

[11] 4,378,371
[45] Mar. 29, 1983

[54] COMBATING FUNGI WITH N-ALKYL-CARBAMIC ACID 1,1,2-TRIMETHYL-5-SUBSTITUTED-INDAN-4-YL ESTERS

[75] Inventors: Horst Peuker, Monheim; Detlef Grotkopp, Duesseldorf; Karlfried Wedemeyer, Cologne; Wilhelm Brandes, Leichlingen, all of Fed. Rep. of Germany

[73] Assignee: Bayer Aktiengesellschaft, Leverkusen, Fed. Rep. of Germany

[21] Appl. No.: 222,194

[22] Filed: Jan. 2, 1981

[30] Foreign Application Priority Data

Jan. 22, 1980 [DE] Fed. Rep. of Germany ....... 3002202

[51] Int. Cl.³ ............................................. A01N 47/10
[52] U.S. Cl. .................................... 424/300; 560/134
[58] Field of Search ........................ 560/134; 424/300

[56] References Cited

U.S. PATENT DOCUMENTS

| | | | |
|---|---|---|---|
| 2,870,057 | 1/1959 | Hartle et al. | 560/134 |
| 3,084,096 | 4/1963 | Lambrech | 560/134 |
| 3,597,472 | 8/1971 | Heiss et al. | 560/134 |
| 3,712,915 | 1/1973 | Seyberlich et al. | 560/134 |

*Primary Examiner*—John F. Terapane
*Assistant Examiner*—Frederick W. Pepper
*Attorney, Agent, or Firm*—Sprung, Horn, Kramer & Woods

[57] ABSTRACT

Fungicidally active N-alkyl-carbamic acid 1,1,2-trimethyl-5-substituted-indan-4-yl esters of the formula

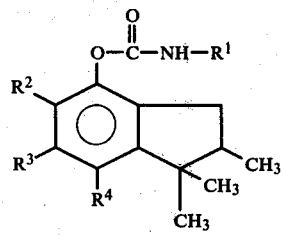

in which
$R^1$ is an alkyl group,
$R^2$ is an alkyl or aralkyl group,
$R^3$ is a hydrogen atom, an alkyl group or a halogen atom, and
$R^4$ is a hydrogen atom, an alkyl group, a halogen atom, or an alkoxy or alkylmercapto group.

2 Claims, No Drawings

COMBATING FUNGI WITH N-ALKYL-CARBAMIC ACID 1,1,2-TRIMETHYL-5-SUBSTITUTED-INDAN-4-YL ESTERS

The present invention provides novel fungicidally active N-alkyl-carbamic acid 1,1,2-trimethyl-5-substituted-indan-4-yl esters of the formula

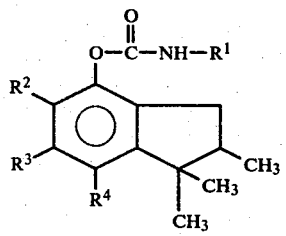

in which
$R^1$ is an alkyl group,
$R^2$ is an alkyl or aralkyl group,
$R^3$ is a hydrogen atom, an alkyl group or a halogen atom, and
$R^4$ is a hydrogen atom, an alkyl group, a halogen atom, or an alkoxy or alkylmercapto group.

Surprisingly, the particular indan-4-yl N-alkylcarbamates of the present invention, which, in contrast to compounds of similar structure which are already known, have, as a common criterion, in each case a methyl group in the 1-, 1- and 2-positions on the indane ring system, exhibit a considerably more powerful fungicidal action than the compounds known from the state of the art.

Preferred compounds of the present invention are those in which $R^1$ represents an alkyl group with 1 to 4 carbon atoms, $R^2$ represents an alkyl group with 1 to 4 carbon atoms or a benzyl radical, $R^3$ represents a hydrogen or halogen atom or a methyl group and $R^4$ represents a hydrogen or halogen atom, an alkyl group with 1 to 4 carbon atoms or a methylmercapto group.

Compounds of the present invention which are of special interest because of their good fungicidal activity are, in particular, those in which $R^1$ and $R^2$ denote methyl groups, $R^3$ denotes a hydrogen or chlorine atom and $R^4$ denotes a hydrogen atom or a methyl group. N-methylcarbamic acid 1,1,2,5-tetramethyl-indan-4-yl ester may be mentioned as an example of such a compound of preferred interest (see Example 1).

According to the present invention there is further provided a process for the production of a compound of the present invention characterized in that:

(a) a 4-hydroxy-indane of the general formula

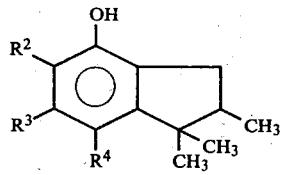

in which:
$R^2$, $R^3$ and $R^4$ have the meaning indicated above, is reacted with an alkyl isocyanate of the general formula $$OCN-R^1 \quad (III)$$

in which
$R^1$ has the meaning indicated above, or, (b) a 4-hydroxy-indane of the general formula (II) is converted into the corresponding chlorocarbonic acid ester with an excess of phosgene in a first stage, and the resulting ester is reacted in a second stage with an alkylamine, or (c) a 4-hydroxy-indane of the general formula (II) is reacted with an equivalent amount of phosgene to give the corresponding bis-(indanyl) carbonate, in a first stage, and this product is split with alkylamine in a second stage.

The course of the reaction in the preparation of the compounds according to the invention can be illustrated by the following examples:

If 4-hydroxy-1,1,2,5-tetramethyl-indane and methyl isocyanate are used as starting substances, the course of the reaction in process variant (a) is illustrated by the following equation:

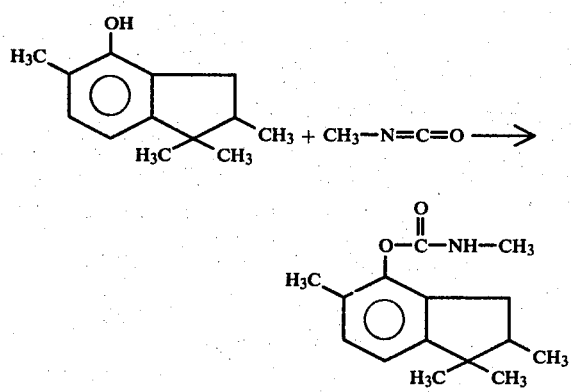

If 4-hydroxy-1,1,2,5-tetramethyl-indane, phosgene and methylamine are used as starting substances, the course of the reaction in process variant (b) is illustrated by the following equation:

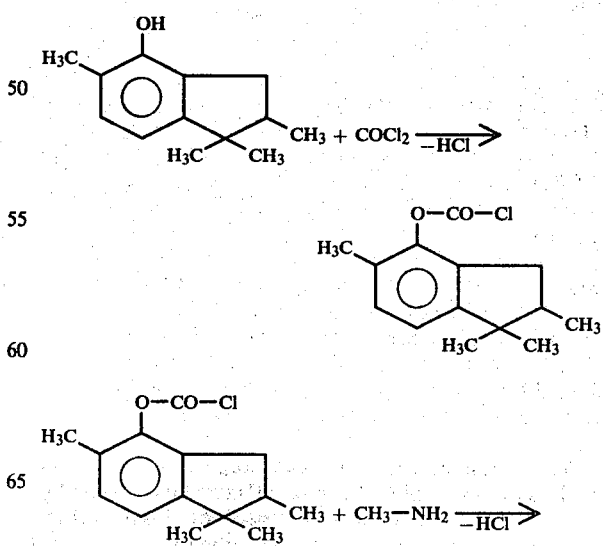

-continued

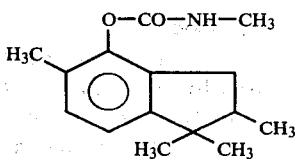

If 4-hydroxy-1,1,2,5-tetramethyl-indane, phosgene and methylamine are used as starting substances, the course of the reaction in process variant (c) is illustrated by the following equation:

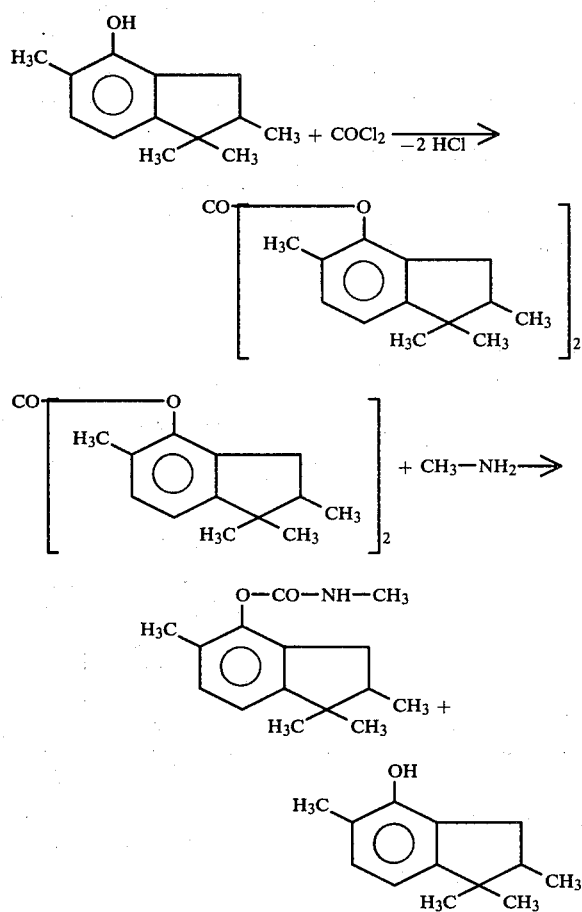

Particularly preferred 4-hydroxy-indanes of formula (II) to be used as starting compounds for the processes of the present invention are those in which $R^2$, $R^3$ and $R^4$ have the meanings indicated above in the case of preferred and particularly preferred compounds of the present invention.

The preparation of the starting substances of the formula (II) is known (compare U.S. patent specification No. 3,057,929). It is effected, for example, by isomerizing the corresponding chromanes in the presence of Friedel-Crafts catalysts. Thus, for example, 4-hydroxy-1,1,2,5-tetramethyl-indane is producible by treatment of 2,2,3,8-tetramethyl-chromane with aluminum-III chloride.

The chromanes used for the preparation of the 4-hydroxy-indanes of the formula (II) can be obtained by reacting phenols, such as o-cresol or 2,4-dimethylphenol, with isoprene (compare Houben-Weyl, "Methoden der organischen Chemie" ("Methods of Organic Chemistry"), 4th edition, Volume 6/1c, page 987–989 (1976)).

Compounds of the formula (II) in which $R^4$ represents halogen can be obtained by halogenating the corresponding substituted 4-hydroxy-indanes. Thus, for example, 7-bromo-4-hydroxy-1,1,2,5-tetramethyl-indane is producible by bromination of 4-hydroxy-1,1,2,5-tetramethyl-indane in glacial acetic acid (see Houben-Weyl, "Methoden der organischen Chemie" ("Methods of Organic Chemistry"), 4th edition, Volume 5/4, page 260 et seq. (1960)).

Compounds in which $R^4$ represents thioalkyl can be prepared by reacting substituted 4-hydroxy-indanes with a free 7-position with a dialkyl disulphide in the presence of a sulphonic acid (see Belgian patent specification No. 627,306), or by thiocyanates of the 4-hydroxy-indanes with thiocyanogen and subsequently saponifying the product (see H. P. Kaufmann and Weber, Arch. Pharm. 267, 192 (1929); and Kohn, M. 58, 73, 78 (1931)). Thus, for example, 7-methyl-thio-4-hydroxy-1,1,2,5-tetramethyl-indane is producible from 4-hydroxy-1,1,2,5-tetramethyl-indane and thiocyanogen.

The starting substances also required for the preparation of the compounds of the formula (I) according to the invention, that is to say phosgene and alkyl isocyanate for process variant (a) and phosgene and alkylamine for process variant (b) and (c), are generally known. Those alkyl isocyanates and alkylamines which contain an alkyl radical with 1 to 4 carbon atoms are preferably used. Examples which may be mentioned here are: methyl isocyanate, ethyl isocyanate and butyl isocyanate, and the following amines: methylamine, ethylamine, isopropylamine, butylamine and isobutylamine.

The compounds of the formula (I) according to the invention can be prepared by process variants (a), (b) and (c) indicated above.

The reaction in process variant (a) can be carried out in inert solvents. Examples of suitable solvents for this are hydrocarbons, such as benzine and benzene, chlorinated hydrocarbons, such as chlorobenzene, and also ethers, such as dioxane, or mixtures of these solvents. The reaction is generally catalyzed by adding a tertiary amine, for example triethylamine or diazobicyclooctane.

The reaction temperatures can be varied within a substantial range. However, the reaction is in general carried out between 0° and 150° C., preferably between 20° and 110° C.

If the reaction is carried out according to process variant (b), the 4-hydroxy-indane of the formula (II) is converted, in the first stage, into the chlorocarbonic acid ester with an excess of phosgene, preferably in the presence of inert solvents, such as aromatic, optionally chlorinated hydrocarbons, and preferably benzene, toluene, xylene or chlorobenzene. The hydrochloric acid formed is bonded by dropwise addition of a base, preferably sodium hydroxide, and the pH value of the reaction solution is thus kept below 7. The reaction is in general carried out at a temperature between −20° and +20° C., preferably between −10° and +10° C. In the second stage, the chlorocarbonic acid ester is reacted, either after isolation or directly in the reaction solution obtained, with an equivalent amount of an alkylamine. This reaction is likewise preferably carried out in the presence of inert solvents, such as aromatic and aliphatic, optionally chlorinated hydrocarbons, such as benzene, chlorobenzene, benzine or carbon tetrachloride, or ethers, such as dioxane. The reaction temperatures can again be varied within a certain range; the reaction is in general carried out between −20° and +20° C., preferably between −10° and +10° C.

Finally, if the reaction is carried out according to process variant (c), the 4-hydroxy-indane of the formula (II) is reacted, in the first stage, with an equivalent amount of phosgene to give the bis-(indanyl) carbonate. The reaction is preferably carried out in inert solvents, such as aromatic hydrocarbons, for example benzene and toluene, the hydrochloric acid formed being bonded by adding a base, preferably an alkali metal hydroxide. The pH value of the reaction solution should be approximately 8. The reaction temperature can be varied within a substantial range, and is in general between 0° and 100° C., preferably between +20° and +60° C. The carbonate formed in the first stage is then split with an alkylamine. This reaction is preferably carried out without a solvent. However, it can also be carried out in solvents. The reaction temperatures are generally between −30° and +40° C., preferably between −10° and +20° C.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The compounds of the formula (I) according to the invention have, in particular, a good action against *Fusicladium dendriticum,* the apple scab causative organism. They also have an activity against *Pellicularia sasakii* in rice plants.

The active compounds can be converted into the customary formulations, such as solutions, emulsions, powders, suspensions, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid of liquefied gaseous diluent or carrier or in admixture with a liquid diluent or carrier containing a surface-active agent.

The present invention also provides a method combating fungi which comprises applying to the fungi, or to a habitat thereof, a compound of the present invention alone or in the form of a composition containing as active ingredient a compound of the present invention is admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

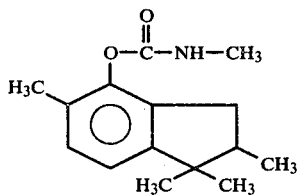

600 g (about 3.16 moles) of 4-hydroxy-1,1,2,5-tetramethyl-indane, 10 ml of triethylamine and 194 g (about 3.40 moles) of methyl isocyanate were dissolved in 3.0 liters of ligroin at room temperature and the solution was then warmed to 80° C. and subsequently stirred at this temperature for about 20 hours. On cooling, the product crystallized out from 55° C. After filtering off and drying, the product was recrystallized from ligroin.

737 g of N-methyl-carbamic acid 1,1,2,5-tetramethyl-indan-4-yl ester of melting point 109.5° to 110.5° C. were obtained.

The yield was 94.5% of theory.

EXAMPLE 2

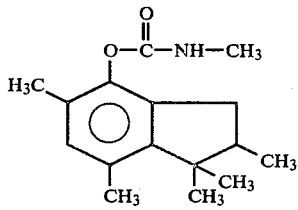

34 g of 4-hydroxy-1,1,2,5,7-pentamethyl-indane, 14.3 g of methyl isocyanate and a few drops of triethylamine were dissolved in 102 ml of ligroin and the solution was stirred under slight reflux (about 70° C.) overnight. After cooling to 30° C., the mixture was stirred with 40 ml of water and the colorless crystals were filtered off and dried. Recrystallization from ligroin and toluene gave 27.7 g of N-methyl-carbamic acid 1,1,2,5,7-pentamethylindan-4-yl ester of melting point 130.5°–131° C.

The following compounds of the general formula

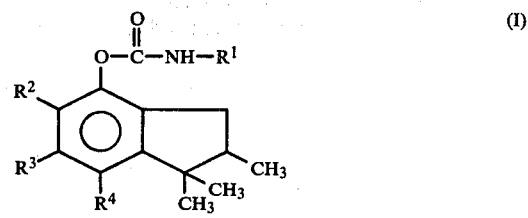

were obtained in a corresponding manner:

| Compound No. | $R^1$ | $R^2$ | $R^3$ | $R^4$ | Melting point (°C.) |
|---|---|---|---|---|---|
| 3 | $CH_3$ | $CH_3$ | Cl | H | 156,5–158,8 |
| 4 | $C_2H_5$ | $CH_3$ | H | H | 64–65 |
| 5 | $i$-$C_3H_7$ | $CH_3$ | H | H | 77–78 |
| 6 | $CH_3$ | $CH_3$ | H | Br | 127–128 |
| 7 | $CH_3$ | $CH_3$ | H | S—$CH_3$ | 104,5–106 |
| 8 | $C_6H_5$ | $CH_2$—$C_6H_5$ | H | Cl | 125,5–126 |
| 9 | $CH_3$ | $C_2H_5$ | H | H | 93–94 |
| 10 | $CH_3$ | $CH_3$ | H | Cl | 105 |
| 11 | $CH_3$ | $CH_3$ | $CH_3$ | H | 116 |

The fungicidal activity of the compounds of this invention is illustrated by the following example wherein the compounds according to the present invention are each identified by the number (given in brackets) from Examples 1 and 2:

EXAMPLE 3

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants then again came into a greenhouse for 14 days.

15 days after inoculation, the infection of the seedlings was determined. The assessment data were converted to percent infection. 0% denoted no infection and 100% denoted that the plants were totally infected.

In this test, for example, the following compounds exhibited a superior action compared with the prior art: compounds (4), (2), (9), (3), (6), (7) and (1).

It will be understood that the specification and examples are illustrative but not limitative of the present invention and that other embodiments within the spirit and scope of the invention will suggest themselves to those skilled in the art.

We claim:

1. A method of combatting fungi comprising applying to the fungi, or to a habitat thereof, a fungicidally effective amount of an N-alkyl-carbamic acid indan-4-yl ester of the formula

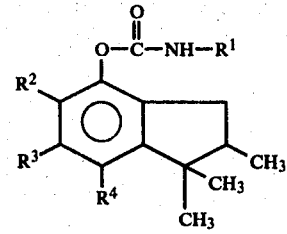

in which
R$^1$ is an alkyl group,
R$^2$ is an alkyl or aralkyl group,
R$^3$ is a hydrogen atom, an alkyl group or a halogen atom, and
R$^4$ is a hydrogen atom, an alkyl group, a halogen atom, or an alkoxy or alkylmercapto group.

2. The method according to claim 1, wherein such compound is N-methyl-carbamic acid 1,1,2,5-tetramethylindan-4-yl ester, N-methyl-carbamic acid 1,1,2,5,7-pentamethylindan-4-yl ester, or N-methyl-carbamic acid 6-chloro-1,1,2,5-tetramethylindan-4-yl ester.

* * * * *